US00PP14481P39

(12) United States Plant Patent
Westhoff

(10) Patent No.: US PP14,481 P3
(45) Date of Patent: Jan. 27, 2004

(54) SUTERA PLANT NAMED 'WESBAVIO'

(50) Latin Name: *Sutera cordata*
Varietal Denomination: Wesbavio

(75) Inventor: Heinrich Westhoff, Südlohn/Oeding (DE)

(73) Assignee: Heinrich Westhoff & Josef Westhoff (DE)

( * ) Notice: Subject to any disclaimer, the term of this patent is extended or adjusted under 35 U.S.C. 154(b) by 0 days.

(21) Appl. No.: 10/037,717

(22) Filed: Jan. 4, 2002

(65) Prior Publication Data

US 2003/0131387 P1 Jul. 10, 2003

(51) Int. Cl.[7] ..... A01H 5/00

(52) U.S. Cl. ..... Plt./263

(58) Field of Search ..... Plt./263

*Primary Examiner*—Bruce R. Campell
*Assistant Examiner*—Susan B. McCormick
(74) *Attorney, Agent, or Firm*—Webb Ziesenheim Logsdon Orkin & Hanson, P.C.

(57) ABSTRACT

A new and distinct early flowering sutera plant with intense violet-blue colored flowers and vigorous growth.

1 Drawing Sheet

Botanical classification: *Sutera cordata.*
Varietal denomination: 'Wesbavio'.

BACKGROUND OF THE INVENTION

The present invention comprises a new and distinct cultivar of Sutera plant known by the varietal name 'Wesbavio'. The new variety was discovered in 2001 in a selected breeding program in Südlohn, Germany. The new variety is a selection from the cross of proprietary unpatented breeding plants. The growth character of the new variety is similar to its parents but with bigger flowers. The new variety was first asexually reproduced in December 2000 by cuttings in Südlohn, Germany. The new variety has been trial and field tested at Südlohn and has been found to retain its distinctive characteristics and remain true to type through successive propagations.

The following traits in combination distinguish 'Wesbavio' as a new and distinct cultivar:

1. Intense colored flowers.
2. Short internodes.
3. Compact growth.
4. Large flowers.
5. Dentate leaf margin.

The new variety has a similar leaf arrangement to the unpatented varieties 'Seamist' and 'Cabane'. However, 'Wesbavio' has more compact branches compared to 'Seamist' and 'Cabane'. The leaves of 'Wesbavio' have a broader dentation on the margins than 'Seamist' and 'Cabane'. The petals of 'Wesbavio' are similar to the compared varieties in arrangement, shape, margin, and apex description.

DESCRIPTION OF THE DRAWINGS

The accompanying photographic drawing illustrates the new variety, with the color being as nearly true as is possible with color illustrations of this type.

DESCRIPTION OF THE PLANT

The following detailed description sets forth characteristics of the new cultivar. The data which defines these characteristics were collected by asexual reproductions carried out in Südlohn, Germany. Plants for the description were 20 weeks old, grown in a greenhouse at 20–25° C. daytime temperature and at 16–18° C. night temperature with light levels of 3,000–50,000 lux. The color readings were taken on a plant outdoors and in a greenhouse under natural light. Color references are primarily to The R.H.S. Colour Chart of The Royal Horticultural Society of London.

PLANT

Classification:
*Botanical.*—*Sutera cordata.*
*Commercial.*—Bacopa.
Form: Hanging with a compact, spherical shape.
Height: 18 cm from soil to top of flowers; 60 cm wide.
Growth: Vigorous.
Roots:
*Habit.*—Fine, well-branched.
*Time to initiate roots.*—About 10 days at 20° C.
*Time to develop roots.*—About 28 days at 20° C.
Main stem: 55 cm long; 1.1 mm diameter; Yellow-Green Group 144A.
Lateral branches:
*Form.*—Hanging.
*Color.*—Yellow-Green Group 144A.
*Texture.*—Pubescent (very short, dense hairs).
*Diameter.*—0.7 mm.
*Length.*—27 cm.
*Internode length.*—1.5 cm.
*Quantity.*—2 per node.
Foliage:
*Arrangement.*—Opposite.
*Number of leaves per branch.*—2 per node.
*Size of leaf.*—Length: 1.27 cm. Width: 1.0 cm.
*Shape of leaf.*—Ovate to elliptic.

*Shape of apex.*—Acute.
*Shape of base.*—Attentuate.
*Texture.*—Smooth.
*Aspect.*—Mostly flat; slightly cupped.
*Margin type.*—Dentate.
*Color.*—Young leaves: Upper surface: Yellow-Green Group 147A-B. Lower surface: Yellow-Green Group 147B. Mature leaves: Upper surface: Yellow-Green Group 147A. Lower surface: Yellow-Green Group 147B.
*Petioles.*—Length: 2.8 mm. Diameter: 0.95 mm. Color: Yellow-Green Group 147A-B.
*Veins.*—Color: Upper surface: Yellow-Green Group 147A. Lower surface: Yellow-Green Group 146C.

FLOWER

Natural flowering season: Spring through autumn until frost; tolerates temperatures of about 4–30° C.
Flower type and habit: Single, salverform, long lasting, persistent.
Average number of blooms per stem: 6–8.
Fragrance: None.
Flower size:
*Diameter.*—1.4 cm.
*Length.*—0.87 cm.
*Tube length.*—0.8 cm.
*Tube diameter.*—Distal end: 0.4 cm. Proximal end: 0.18 cm.
Corolla:
*Petal length from throat.*—6 mm.
*Petal width.*—4 mm.
*Petal quantity.*—5, fused.
*Petal apex shape.*—Obtuse.
*Texture.*—Satiny.
Color:
*Petals.*—When opening: Upper surface: Violet-Blue Group 90C. Lower surface: Violet-Blue Group 94C. Fully opened: Upper surface: Between Violet-Blue Group 90D and Violet Group 85A, changing to Violet-Blue Group 90D over time. Lower surface: Violet Group 85B-C.
*Flower throat inside surface.*—Orange Group 25A; not veined.
*Flower tube.*—Outside: Tip: Violet-Blue Group 92D. Middle: Yellow-Orange Group 23A. Base: Yellow-Green Group 150C. Veins: Not veined.
Peduncle:
*Length.*—1.1 cm.
*Diameter.*—0.5 mm.
*Color.*—Yellow-Green Group 144A.
*Orientation.*—Acute angle.
*Strength.*—Flexible.
Bud:
*Shape.*—Oblanceolate.
*Length.*—6.7 cm.
*Diameter.*—2.4 mm.
*Color.*—Tip: Violet-Blue Group 97B-D. Middle: Yellow-Orange Group 21A. Base: Yellow-Green Group 150C.
Calyx:
*Arrangement.*—Whorled.
*Length.*—5 mm.
*Diameter.*—2 mm.
*Sepals.*—Shape: Needle. Width: 0.7 mm. Length: 4.8 mm. Margin: Entire. Texture: Pubescent. Color: Upper surface: Yellow-Green Group 146A. Lower surface: Yellow-Green Group 146A.

REPRODUCTIVE ORGANS

Stamens:
*Number.*—4; on two plains (2 high, 2 low); fused with petals.
*Filament length.*—4 mm and 2 mm.
*Anthers.*—Shape: Flat, shaped liked beans. Length: 0.8 mm. Width: 1 mm. Color: Yellow-Orange Group 21A.
*Pollen.*—Color: Yellow-Orange Group 21A. Amount: Moderate.
Pistil:
*Length.*—1.1 cm.
*Style.*—Length: 0.75 cm. Color: Yellow-Green Group 154C.
*Stigma.*—Shape: Long; curved inwardly. Color: Yellow-Green Group 144C. Ovary color: Yellow-Green Group 144B.
Seeds: Generally none.
Disease/pest resistance: No unusual susceptibility to diseases or pests has been noted to date.

I claim:

1. A new and distinct variety of Sutera plant substantially as shown and described.

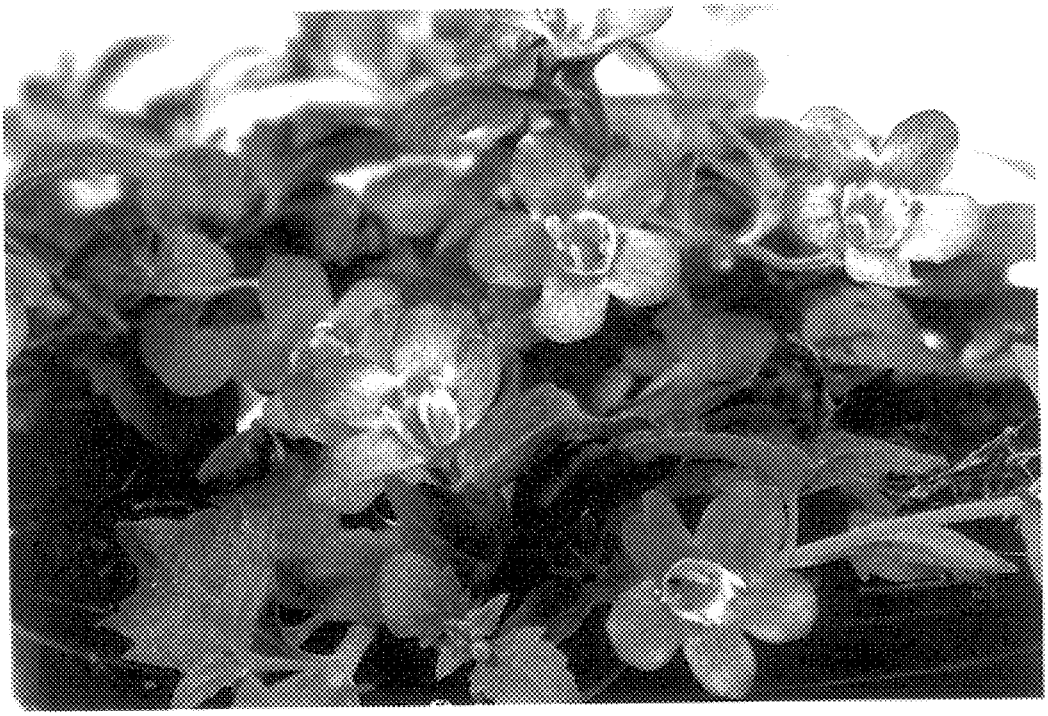

* * * * *